United States Patent
Terzini et al.

(10) Patent No.: US 9,665,688 B2
(45) Date of Patent: May 30, 2017

(54) PRODUCT DISPENSING SYSTEM AND METHOD WITH REDUNDANT CONTAINER INDUCTION

(71) Applicant: Tension International, Inc., Kansas City, MO (US)

(72) Inventors: Robert Terzini, Corinth, TX (US); Brian Sullivan, Grosse Point, MI (US)

(73) Assignee: Tension International Inc., Kansas City, MO (US)

( * ) Notice: Subject to any disclaimer, the term of this patent is extended or adjusted under 35 U.S.C. 154(b) by 511 days.

(21) Appl. No.: 13/895,318

(22) Filed: May 15, 2013

(65) Prior Publication Data

US 2013/0310969 A1    Nov. 21, 2013

Related U.S. Application Data

(60) Provisional application No. 61/647,500, filed on May 15, 2012.

(51) Int. Cl.
*G06F 19/00* (2011.01)
*G06Q 10/08* (2012.01)
*G06Q 50/22* (2012.01)

(52) U.S. Cl.
CPC ....... *G06F 19/3462* (2013.01); *G06Q 10/087* (2013.01); *G06Q 50/22* (2013.01)

(58) Field of Classification Search
CPC .. G06F 19/00; G06F 17/0092; G06F 19/3456; G06F 19/3462; G06Q 50/22; G06Q 10/08

USPC .............. 198/347.1, 347.4; 700/213–230
See application file for complete search history.

(56) References Cited

U.S. PATENT DOCUMENTS

| | | | | |
|---|---|---|---|---|
| 5,208,762 A | * | 5/1993 | Charhut | A61J 7/0084 221/9 |
| 5,414,974 A | * | 5/1995 | Van de Ven | B65B 25/14 53/168 |
| 5,623,415 A | * | 4/1997 | O'Bryan | G01N 35/021 198/617 |
| 5,771,657 A | * | 6/1998 | Lasher | B65B 61/20 53/131.4 |

(Continued)

*Primary Examiner* — Gene Crawford
*Assistant Examiner* — Stephen Akridge
(74) *Attorney, Agent, or Firm* — Polsinelli PC; Marcia J. Rodgers; Derek D. Donahoe (57) ABSTRACT

A system for dispensing product-filled containers in which the containers are filled prior to labeling, so that any container may filled at any dispensing station. The system includes multiple dispensing stations, both manual and automated, disposed adjacent a conveyor. Automated dispensing stations include quantities of products, fillable product containers, and a labeling assembly. Each dispensing station dispenses a predetermined quantity of products into a container and labels the container for transport via an exit conveyor to the main conveyor. Carriers are delivered via the main conveyor into a container carrier queue lane, where a sensor reads the RFID before a filled, labeled container is deposited into the carrier. A sensor reads the label bar code and transmits the bar code and RFID information to the computer database, mating the carrier with the filled container. System software load balances the components of an order by routing them to different dispensing stations.

17 Claims, 5 Drawing Sheets

(56) References Cited

U.S. PATENT DOCUMENTS

| | | | | |
|---|---|---|---|---|
| 5,988,858 | A * | 11/1999 | Yuyama | B65G 1/1376 |
| | | | | 700/213 |
| RE37,829 | E * | 9/2002 | Charhut | A61J 3/002 |
| | | | | 221/9 |
| 6,622,127 | B1 * | 9/2003 | Klots | G06F 17/30902 |
| | | | | 705/22 |
| 6,999,847 | B2 * | 2/2006 | Barry | B25J 18/04 |
| | | | | 198/346.1 |
| 7,313,460 | B1 * | 12/2007 | Prater | G06Q 10/087 |
| | | | | 700/213 |
| 7,748,199 | B2 * | 7/2010 | Sankaran | B65B 5/045 |
| | | | | 53/131.4 |
| 7,765,776 | B1 * | 8/2010 | Leu | B65B 5/045 |
| | | | | 53/131.4 |
| 9,367,981 | B2 * | 6/2016 | Szesko | |
| 2004/0065053 | A1 * | 4/2004 | Rice | B65B 5/103 |
| | | | | 53/445 |
| 2005/0171813 | A1 * | 8/2005 | Jordan | G06Q 50/22 |
| | | | | 705/2 |
| 2009/0173779 | A1 * | 7/2009 | Szesko | G06F 19/3462 |
| | | | | 235/375 |
| 2009/0287350 | A1 * | 11/2009 | Johnson | G06F 19/3462 |
| | | | | 700/236 |
| 2010/0010666 | A1 * | 1/2010 | Adams | E05G 1/06 |
| | | | | 700/231 |
| 2010/0089997 | A1 * | 4/2010 | Carson | G07F 9/026 |
| | | | | 235/375 |
| 2011/0146212 | A1 * | 6/2011 | Terzini | A61J 7/0084 |
| | | | | 53/467 |
| 2013/0151005 | A1 * | 6/2013 | Gerold | G06F 19/3462 |
| | | | | 700/235 |

* cited by examiner

PRODUCT DISPENSING SYSTEM AND METHOD WITH REDUNDANT CONTAINER INDUCTION

CROSS-REFERENCE TO RELATED APPLICATIONS

This application claims priority under 35 U.S.C. 119(e) and 37 C.F.R. 1.78(a)(4) based upon U.S. Provisional Application Ser. No. 61/647,500 for REDUNDANT INDUCTION DISPENSING SYSTEM filed May 15, 2012, the entirety of which is incorporated herein by reference.

FIELD

The present disclosure generally relates to an automated product dispensing system and method. More particularly, it concerns a system and method for dispensing products by induction of empty containers into multiple dispensing stations, both automated and manual.

BACKGROUND

Figure 1:
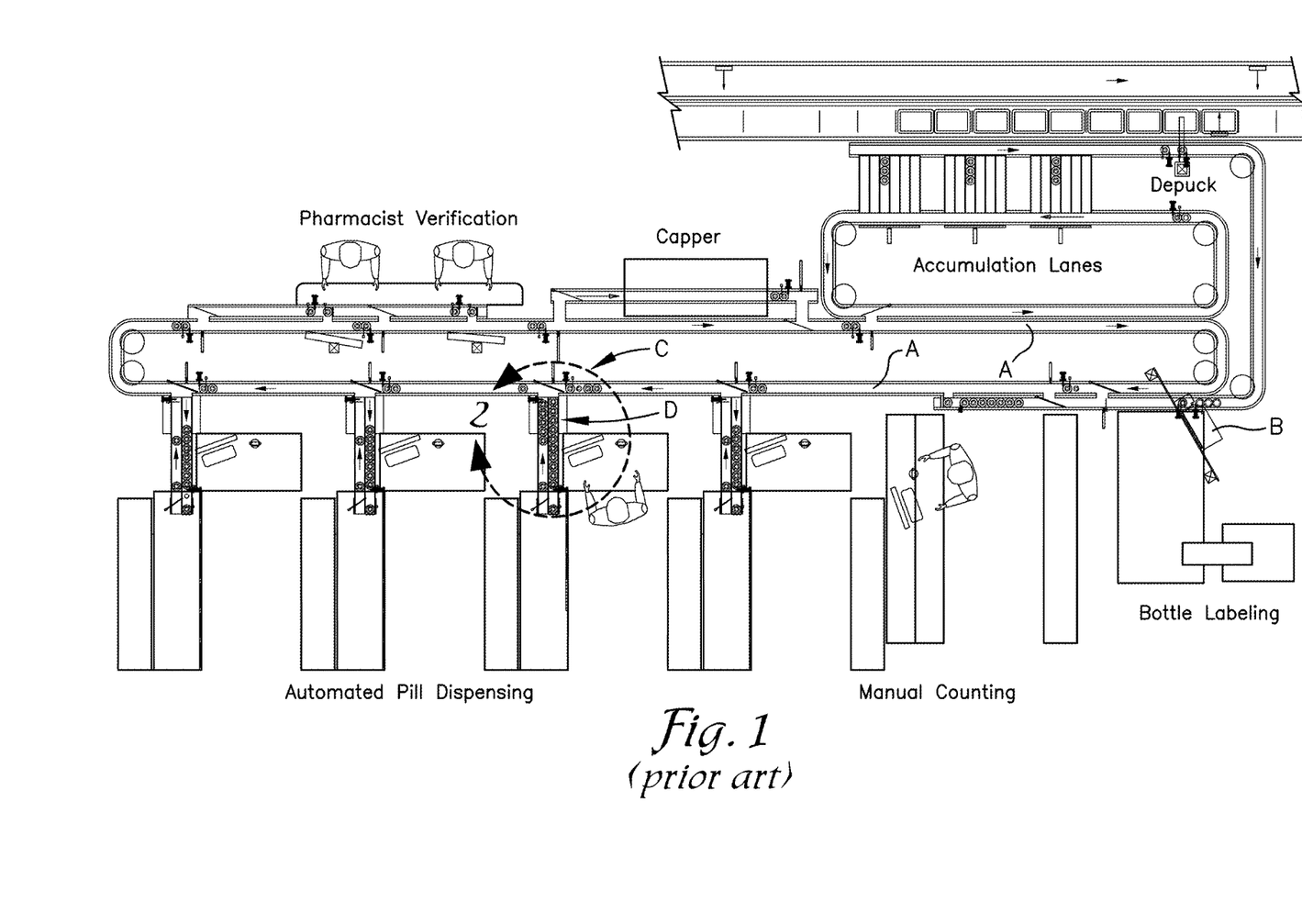
FIG. 1 is a top plan view of a portion of a conventional single induction point system.

Current automated product dispensing systems, such as prescription dispensing systems and the like, generally employ a transporting conveyor which receives empty containers such as bottles or vials. A portion of such a conventional system is depicted in FIG. 1 to include a conveyor A and a labeling station B where the containers are labeled prior to passing to a dispensing station C where they are filled. These systems rely on one or two induction points at an independent container unscrambling or labeling station. At the induction point, empty containers are loaded into an unscrambling assembly which orients them for labeling. A labeling unit such as station B then applies an order-specific label to each empty container, and the labeled containers are deposited onto a conveyor, such as A, for transport to a dispensing station C. In the case of prescription dispensing systems, the label includes patient-specific information. Alternatively, a bar code on the labeled container may be read and matched or "married" by a computer to a carrier or puck equipped with a radio frequency identification (RFID) device. Thereafter, the computer database associates the RFID device of the carrier with the bar code label on the container. The carrier with its mated container is then deposited onto a conveyor for transport to a dispensing station. Once labeled and mated with a carrier, the container proceeds via conveyor to a designated manual or automated dispensing station that contains a supply of the product designated on the label. Each dispensing location is provided with a respective dispensing unit that is equipped with structure such as a spout for dispensing objects or medication in the form of pills, tablets, gel caps or any other suitable "countable" unit. The objects or medications may be pre-counted by dispensing into a temporary holder unit or receiver which discharges its pre-counted contents into the container, or they may be counted as they are dispensed directly into the container. The filled container, or filled container with mated carrier puck, is then passed onto a conveyor for further processing. The container label bar code or carrier RFID is verified by computer comparison of the encoded information with order information contained in a computer database. If verification is satisfactory, the product container is then sealed and/or capped. Depending on the number of items in an order, these completed containers may be individually packed for shipping or accumulated with other containers in an order accumulation device and then packed for shipping.

Figure 2:
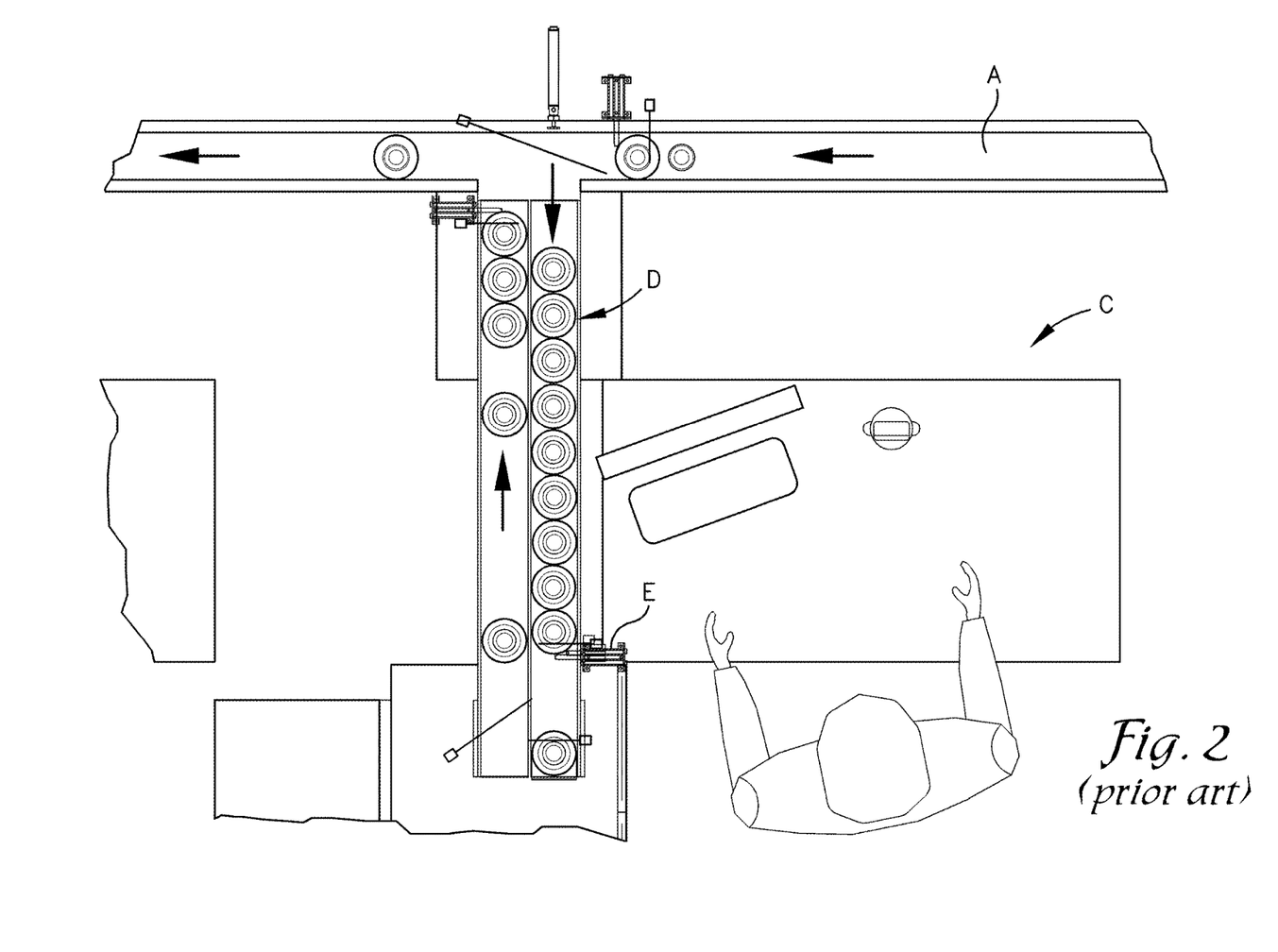
FIG. 2 is an enlarged view showing details of an automatic dispensing station of the system of FIG. 1.

These prior systems thus divert the labeled containers or labeled containers with married carriers into a designated area where they form a queue, such as queue D shown in FIGS. 1 and 2, at the dispensing unit E having a supply of the objects or medications indicated on the label for the container to be filled. This dedicated dispensing unit then dispenses the preselected object or pharmaceutical into the container. If a labeled container or married carrier with labeled container are destined for a particular dispensing unit and the queue for that dispensing unit is full, however, the container or carrier with container must recirculate in the master lane and return to the same dispensing unit several minutes later. In some cases, the vial and carrier must recirculate through the system more than once because, by the time they return to the dispensing unit queue, the queue is full. These traffic flow problems inevitably cause gaps in product dispensing, during which time no container or puck with container is present and the dedicated dispensing unit is required to wait for arrival of the next fillable container. This prevents the dispensing units from continuous dispensing and impairs the overall efficiency of the system.

Accordingly, there is a need for a product dispensing system and method that allows induction of fillable containers into the system for filling at multiple fill points, enabling continuous dispensing of products from automated and manual dispensing units, that greatly improves traffic flow by shortening queues, minimizes recirculation of vials and carriers on the main line, and that minimizes the potential for single points of failure at common labeling and induction assemblies.

SUMMARY

The present disclosure provides a greatly improved system and method for dispensing product-filled containers in which the containers are filled prior to labeling, so that any container may be inducted into any dispensing location for filling in the dispensing system. The system includes a plurality of dispensing locations disposed adjacent a main transporting conveyor. Both manual and automated dispensing stations are provided. Automated dispensing stations each include a quantity of fillable product containers, a quantity of products such as a dispensable medication, and a labeling assembly. Each dispensing station dispenses a predetermined quantity of products into a container and then labels the container and a dispensing station exit conveyor transports the filled, labeled container onto the main conveyor. Carriers may be delivered via the main conveyor into a puck queue lane where a sensor reads an embedded RFID code before a labeled, filled container is placed in the carrier. A sensor reads the container label bar code and the information from the bar code and RFID is transmitted to a computer and entered into an associated database, mating the carrier with the filled container. The system software load balances the various components of each customer order by routing them to different dispensing stations according to pre-arranged rules of the dispensary.

Various objects, features and advantages of this disclosure will become apparent from the following detailed description taken in conjunction with the accompanying drawings, which depict, by way of illustration and example, certain embodiments of this system.

The drawings constitute a part of this specification, include exemplary embodiments of the redundant induction dispensing system, and illustrate various objects and features thereof.

DETAILED DESCRIPTION

Selected embodiments of the present invention are disclosed with reference to the drawings. However, the disclosed embodiments are provided for illustration only and are merely exemplary of the system and method, which may be embodied in various forms. Therefore, specific structural and functional details which are disclosed are not to be interpreted as limiting, but merely as a basis for the claims and as a representative basis for teaching one skilled in the art to variously employ the redundant induction system.

Figure 3:
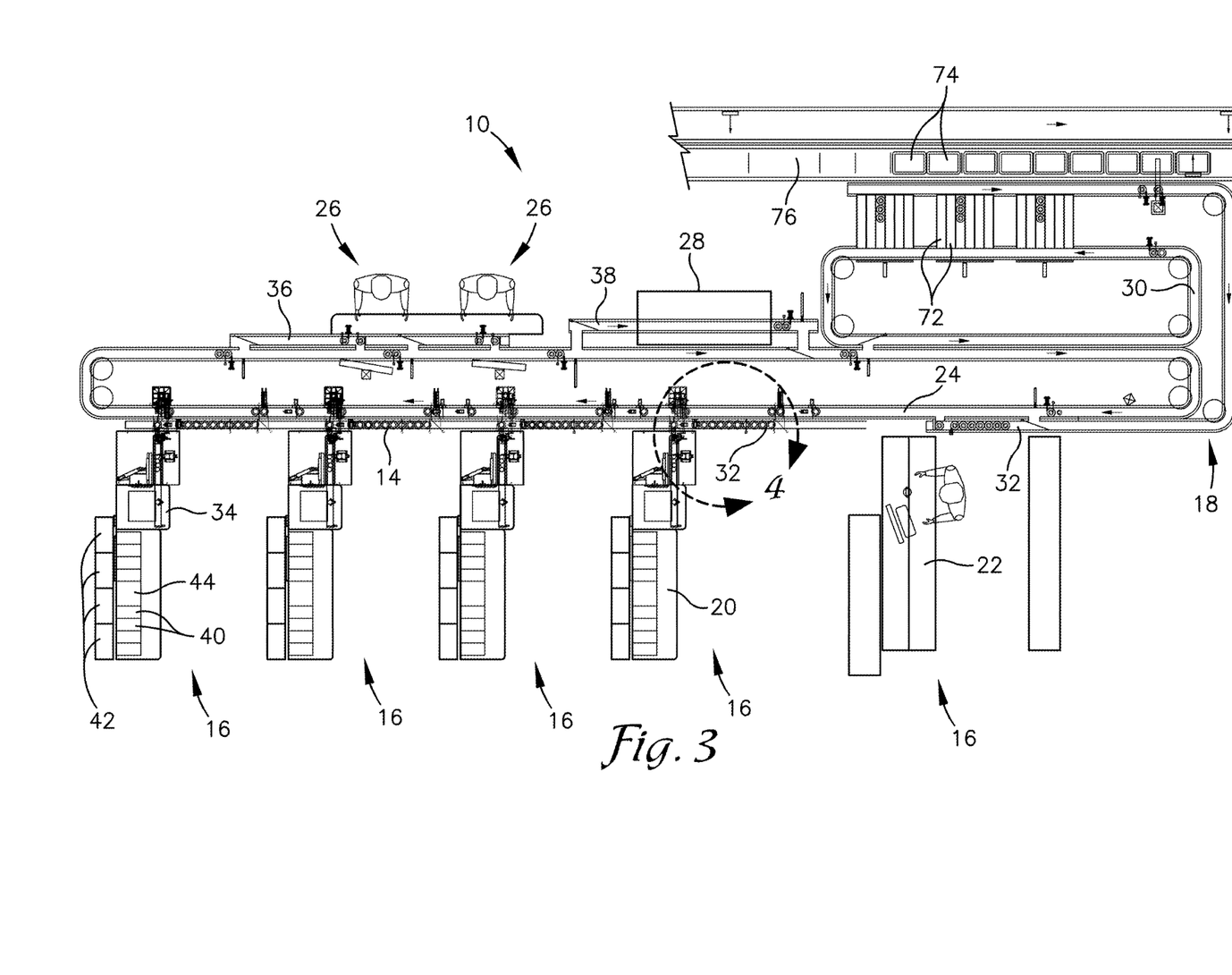
FIG. 3 is a top plan view of a redundant induction system in accordance with the present disclosure.
Figure 4:
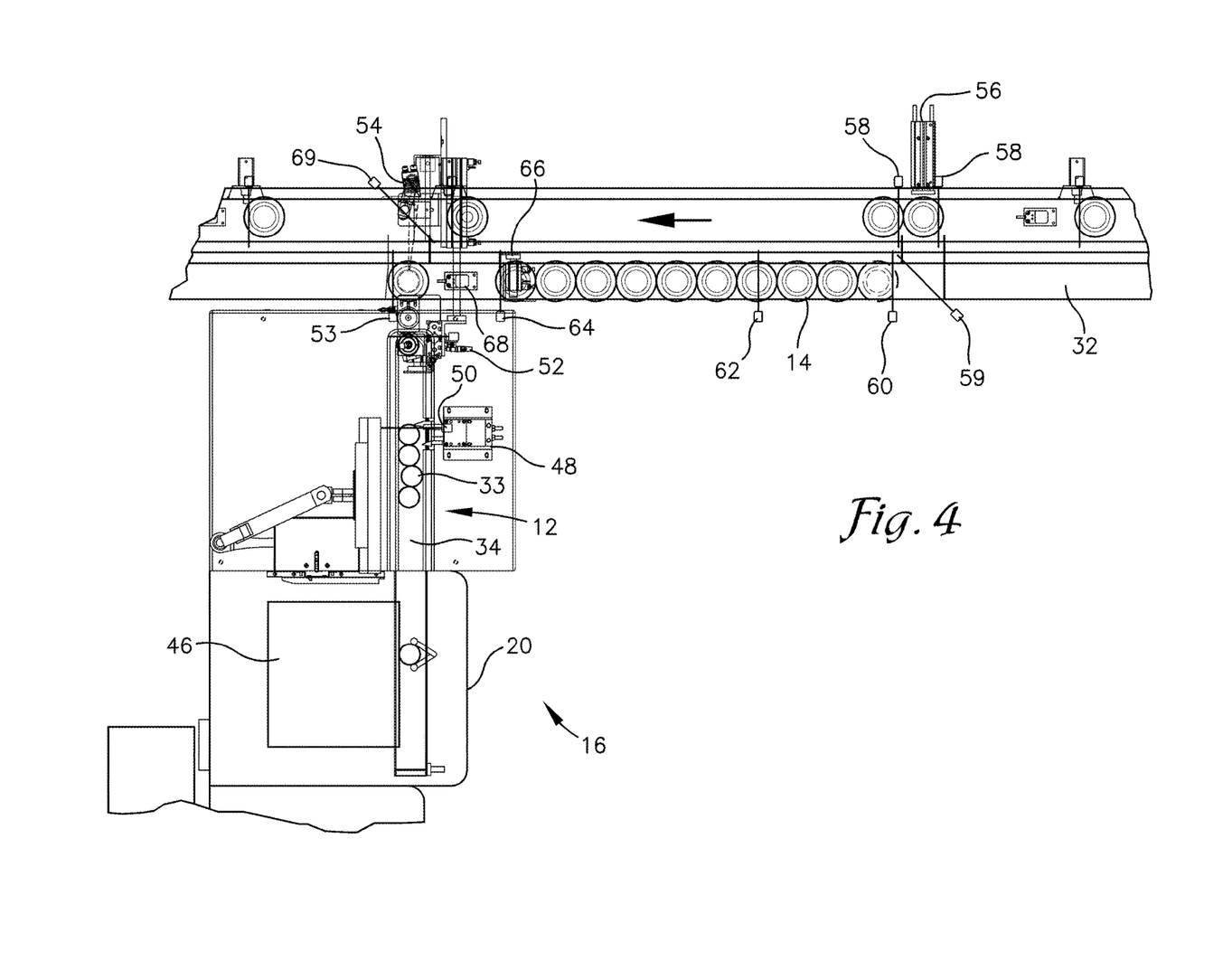
FIG. 4 is an enlarged view showing details of an automatic dispensing station of the system of FIG. 3.

As shown in FIGS. 3 and 4, a product dispensing system with redundant container induction 10 is illustrated in accordance with a first disclosed embodiment. The system 10 dispenses counted products, such as small objects, pharmaceuticals and the like, into containers 12, which may be loaded into individual container carriers or pucks 14 to facilitate transport throughout the system. The dispensing system 10 is advantageous in that it does not induct the containers by pre-labeling and mating them to respective carriers prior to dispensing the products into the containers. Instead, labeling equipment is disposed at each dispensing location for application of a label to the container after dispensing.

The system 10 includes a plurality of dispensing locations 16, disposed in spaced relation adjacent a conveyor transport assembly 18, and a control system 19. Each dispensing location 16 includes an automated dispensing station 20 or a manual dispensing station 22. The system 10 distributes empty carriers 14 equipped with RFID chips to the dispensing stations 20 and 22 with no customer or patient order or prescription assignment until the point of dispensing (FIG. 4).

The conveyor assembly 18 includes a main conveyor lane 24 that forms a loop between the dispensing locations 16, a verification station 26, a capping station 28 and an accumulation loop 30. The conveyor assembly also includes a plurality of container carrier queue lanes 32, one disposed adjacent each dispensing location 16, to receive carriers 14 that are diverted from the main conveyor lane 24 to receive filled containers 12. An exit conveyor 34 is provided adjacent each automated dispensing station 20 for transporting the filled containers through the dispensing station and into the main conveyor lane 24. A downstream verification lane 36 routes the filled containers from the main conveyor lane 24 to the verification station 26 and then back to the main conveyor lane 24 following verification. Further downstream, a capping lane 38 routes the verified, filled containers from the main conveyor lane 24 to the capping station 28 and then back to the main lane 24 after they are sealed and/or capped. Still farther downstream, the filled and capped containers 12 are routed to the accumulation loop 30.

The automated dispensing stations 20 each include a plurality of dispensing modules or cells 40, each including a product magazine 42 for dispensing a selected quantity of a product. This enables each dispensing station 20 to dispense a variety of products. Each dispensing station 20 also includes a bulk container hopper or combination hopper and bottle orientator 44 for temporary storage of a quantity of containers 12 at the station 20. The hopper 44 is conveniently disposed for discharging containers 12 as needed for filling by the adjacent dispensing modules. In one embodiment, pick-and-place structure, which may include a gripper, picks an empty container released from the container hopper 44, fills it with a selected quantity of a product dispensed from the product magazine 42 of a selected dispensing module 40, and deposits the filled container on the dispensing cell exit conveyor 34. In another embodiment, each automatic dispensing module 40 includes structure that receives an empty container from a remote location for filling.

The automatic dispensing stations 20 each include a printer applicator or labeler 46 disposed in adjacent relation to the exit conveyor 34. The printer applicator prints and applies a label to each passing filled container 12. The label includes a bar code containing information regarding the product contents and quantity, as well as any other order or patient-specific information supplied by the control system 19. As best shown in FIG. 4, a singulator 48 equipped with a sensor 50 singulates passage of the filled containers one at a time along the exit conveyor 34. A pick and place unit 52 is disposed adjacent the end of the exit conveyor 34 and in spaced relation to the container carrier queue lane 32. The unit 52 includes a gripper arm configured to grasp each filled container 12 as it reaches the output end of the exit conveyor 34, elevate it, and shift it inboard, over the center of the carrier queue lane 32. A carrier sensor 53 is disposed on or adjacent the outboard sidewall of the carrier queue lane to verify that a puck is in position for receiving the filled container 12. The unit 52 also includes structure for rotating or spinning the gripped container so that its label may be scanned by a bar code reader 54. The bar code reader 54 is disposed at the inboard perimeter of the main conveyor lane 24 and is oriented to pass a beam across the main lane 24 and into the carrier queue lane 32, where it reads the container label bar code.

Once a specified quantity of a selected product has been dispensed into an empty container 12 and the container has been labeled and scanned, it is ready to be mated with a container carrier or puck 14 for conveyor transport to the verification and capping stations 26 and 28 and to the accumulation loop 30 for assembling a complete product order for packaging and shipping. As previously discussed, a carrier queue lane 32 is disposed adjacent each automated and manual dispensing station 20 and 22 for providing a ready supply of empty carriers 14 to receive filled containers from the respective dispensing stations. The inboard sidewall of the main conveyor lane 24 includes a series of cylinders 56, disposed adjacent the entry points of each carrier queue lane 32. These cylinders may be actuated by the control system 19 to push carriers from the main lane into a respective adjacent container queue lane 32. Each cylinder 56 is equipped with carrier sensors 58, positioned on or adjacent the inboard wall of the main lane and adjacent the cylinder. These sensors 58 each project an optical beam that is broken by the passage of a carrier in the main lane into the path of the cylinder 56. A third sensor 59 is positioned on or adjacent the outboard wall of the queue lane and projects a diagonal optical beam that is broken by the passage of a carrier from the main lane to the queue lane, thus serving to verify that the carrier has been pushed from the main lane 32 into the queue lane 32. The outboard sidewall of the queue lane is also provided with a "high water" limiter sensor 60 that determines when the queue lane 32 has reached capacity, and a "low water" limiter sensor 62 that determines when the supply of empty carriers 14 in the lane has reached a predetermined minimum level, so that the control system 19 can instruct actuation of the cylinder 56 to push additional container carriers into the container queue lane 32. The carriers 14 are transported by the queue transport conveyor to a stop sensor 64 that transmits a signal to actuate a stop 66.

Empty carriers 14 are transported along the queue conveyor lane 32 for positioning below a filled and labeled container that has been picked from a respective dispensing station exit conveyor 34. As the carrier passes by in the queue lane, an RFID sensor or passive reader 68 scans the carrier's embedded RFID chip. The bar code reader 54 and the RFID reader 68 transmit their scanned information to the control system 19, where the product label bar code is associated with the carrier RFID in the computer database. In this manner, the filled container 12 and the carrier are mated 14 in the computer database and the filled container and its corresponding carrier are "inducted" into the system. Thereafter, a scan of the carrier RFID may be used to route and track the carrier 14, its container 12, and the contents through the system 10 and to retrieve information from the database regarding the order for use in controlling and verifying the carrier and its container and contents. The mated carrier and container are pushed by a cylinder (not shown) from the queue lane into the main conveyor transport lane. A sensor 69 is positioned on or adjacent the inboard sidewall of the main lane and is positioned diagonally, so that it senses when the mated puck is pushed into the main lane 24.

The sensors 50, 53, 55, 58, 59, 60-, 62, 69, described herein for detecting the presence or absence of a container or carrier may be laser sensors or other light emitting sensor that emits a beam of light that is reflected off a reflective surface back to the sensor. In general, the sensor detects when an object interrupts the reflected beam. In operation, the control unit 78 may activate or retrieve information from a sensor. The control unit 78 determines if the sensor detects the reflected emitted beam, thereby indicating the presence or absence of the object, such as a container or carrier, to be sensed. In response, a notification signal may be provided by the control unit 78 to the computer 80 or user interface 82 to initiate a responsive action, such as advancing the filled containers on the exit conveyor 34 in the direction of the container queue lane and main conveyor lane. Such an analysis may be performed each time a particular action occurs, such as picking a filled container from the dispensing station exit conveyor lane 34, or it may be performed routinely to verify the presence or absence of an object, such as a container carrier, in the location of the sensor beam.

As shown in FIG. 3, the system 10 may also include one or more manual dispensing stations 22, each including one or more product magazines, a container hopper, and a label printer, all of conventional construction. A technician performs the tasks of obtaining a container 12 from the hopper, counting out a selected number of products from a product magazine into the container 12, printing a label and applying it to the container 12. The technician may employ a handheld or fixed bar code scanner to scan the bar coded label of the filled container. The technician also obtains a container carrier from the adjacent carrier queue lane 32, scans the RFID, and deposits the mated container and its carrier onto the main conveyor lane 24 to proceed for further processing.

The filled product containers and their mated carriers are transported via the main conveyor lane to the verification lane 36, which routes them to the verification station 26, where a technician or pharmacist verifies that the contents match the information on the label. They are then routed back to the main conveyor lane, and on to the capping lane 38, which routes them to the capping station 28, where the filled containers 12 are capped, and optionally may be sealed as well. They are then routed back to the main conveyor lane, and on to the accumulation loop 30, where they are scanned and shunted into accumulation lanes 72. When all of the components of an order have been collected in an accumulation lane 72, the carriers are removed and the filled containers deposited into a tote 74, which is transported along a tote conveyor lane to packaging and shipping stations.

Figure 5:
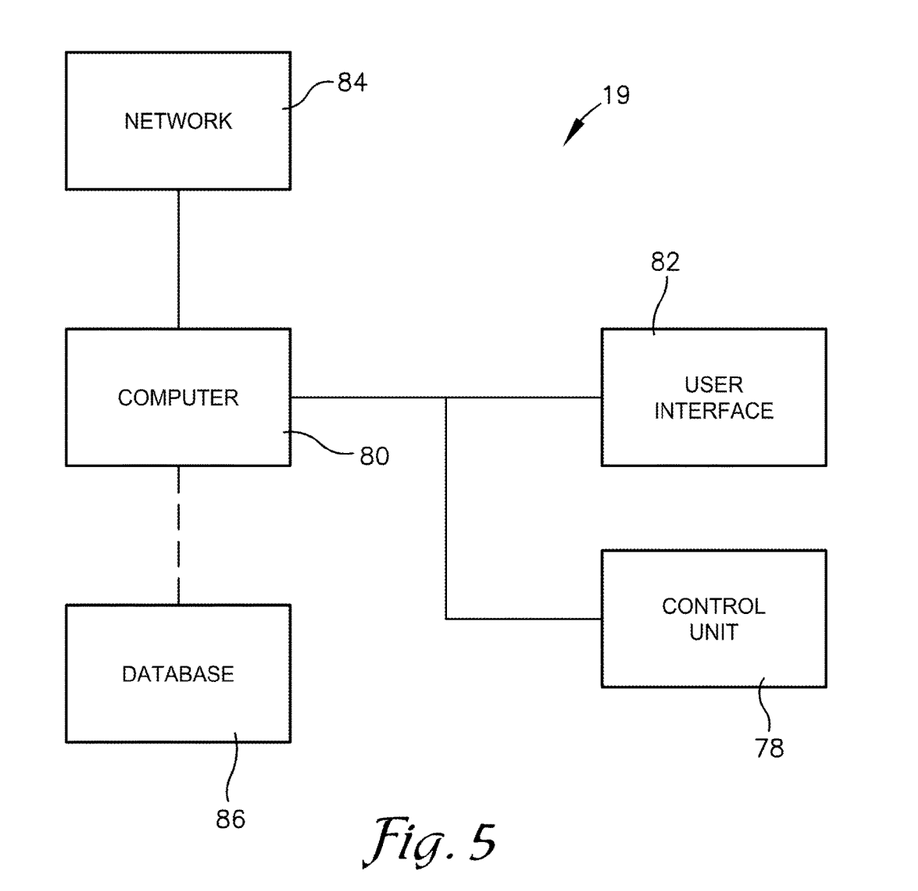
FIG. 5 is a block diagram of a control system of the redundant induction system.

Operation of the various components of the automatic dispensing system with redundant induction of containers is coordinated by the control system 19 to achieve optimum speed, efficiency and accuracy. As shown in FIG. 5, the control system 19 includes a control unit 78 in communication with a computer 80 having a user interface 82. The control unit 78 is in electrical communication with the dispensing system 10 via wired and/or wireless communication. The user interface 82 may be a hand-held device in wired and/or wireless communication with the control unit 78 of the dispensing system. The user interface 82 provides means for a user to control operation of the dispensing system 10, for example, entering parameters or commands for processing by the control unit 78. The control unit 78 uses a programmable logic controller or other control system to process communications and control operations of components of the dispensing system 10.

In one embodiment, a computer 80 or other personal computing device may be used in place of or in conjunction with the user interface 82 to communicate with the control unit 78. The computer 80 (as well as user interface and control unit 78) may include one or more processors for executing one or more computer-readable programs. To facilitate operation, the components may also include a memory controller for interfacing a main memory with the one or more processors for retrieving information, such as instructions of a program, and/or storing information used by the system. The control system 19 may also include an input/output (I/O) interface to interface I/O devices with the processors. I/O devices may also include an input device (not shown), such as an alphanumeric input device, including alphanumeric and other keys for communicating information and/or command selections to the processors. Another type of user input device includes cursor control, such as a mouse, a trackball, or cursor direction keys for communicating direction information and command selections to the processors and for controlling cursor movement on the display device.

The computer 80 may include a dynamic storage device, referred to as main memory, or a random access memory (RAM) or other computer-readable devices for storing information and instructions to be executed by the processors. Main memory also may be used for storing temporary variables or other intermediate information during execution of instructions by the processors. In addition, the computer 80 may be connected to a network 84 through one or more network communication ports to provide information to or receive information from the network. In one embodiment, the network is the Internet and the network communication port includes an Internet modem. The computer may also receive information, such as information concerning a product associated with the dispensing system 10, which may be used by the system during dispensing of one or more products. Alternatively, or in conjunction with the network 84, the computer may be in communication with one or more databases 86 to store information concerning the dispensing system 10.

Advantageously, the system 10 routes empty carriers 14 to the dispensing stations 20 and 22 with no order or prescription information until the point of dispensing. This allows the system to balance incoming queues easily with unassigned carriers and to fill queues solely based on availability of space. This avoids the need for recirculation of carriers that cannot gain entrance to a queue for a specific product, object or medication.

In one exemplary method of use, the system 10 is employed in a high output pharmacy. A series of prescription orders is received in the pharmacy and entered into the control system computer 80, which transmits or forwards them to the database 86 server. Using stored procedures or a similar approach to a database interface, software and controls access and acquire the data to dispense medications to fill the orders. All orders for "countable" products such as tablets, pills, capsules or the like are sent to a countables subsystem that balances the orders and sends them to each of the dispensing stations 20 and 22. At the dispensing stations 20 and 22, the orders are queued up and dispensed in accordance with the assigned priorities of the system. For example, patient orders may be balanced across multiple dispensing stations to allow for concurrent dispensing of multiple prescription components of an order for a single patient. Orders may also be balanced to optimize throughput at each station to provide maximum throughput of the automated and manual dispensing stations, 20 and 22. The priorities may also include issues such as urgency, which may be assigned for walk-up patients, overnight or refrigerated medications, distant locations or any other suitable assigned priority. By sending the prescription orders to each dispensing station 20 and 22 in a balanced fashion for concurrent induction of filled containers into the system 10, every dispensing station becomes available for concurrent dispensing and induction of a filled container bearing one component of the patient prescription order.

It is foreseen that, in addition to automated dispensing station prescription order queues, the system may also utilize manual prescription order queues. Such a manual queue may be established but require the presence of a technician at a station to enter a command at a user interface 82 in order to actuate the dispensing process.

At an automated dispensing station 20, containers 12 may be filled, labeled, and may queue up, for example, in a first-in-first-out exit conveyor lane 34 or on an order collation table, before container carriers 14 arrive at the dispensing station. This decreases dispensing time and increases throughput. For example, a pharmacy with ten automated dispensing stations and one manual station may count and dispense 100 prescriptions into containers 12 and label the filled containers to await mating with a container carrier 14, all before any container carrier arrives at the container carrier queue lane 32 for the dispensing station.

A manual dispensing technician may arrive at a manual dispensing station to find the database server showing a queue of 320 prescription orders to be filled. This enables the technician to stage higher volume prescriptions for that day in quick pick locations because the order mix is known ahead of time.

A plurality of empty container carriers 14 with RFID chips is loaded into the main lane of the conveyor transport assembly 18. As the container carriers advance through the system 10, one or more sensors detects an empty carrier and diverts it into a carrier queue lane 32 at a manual dispensing station 22. A second carrier continues on the main lane and sensors detect the empty carrier and divert it to the first automated dispensing station queue. A third carrier continues downstream and, as it passes the first automated dispensing station queue, sensors detect the empty carrier. Because there is no room in the queue lane 32, however, the carrier is not diverted. Instead, it continues down to the next automated dispensing station queue lane 32 and is diverted into that queue lane where there is room for it.

This differs from prior systems in which each of the carriers is assigned to a specific dispensing point or station. In conventional dispensing systems, manual dispensing station technicians are unaware of the identity of the medications to be dispensed until the designated carrier arrives. A carrier destined for an automated dispensing station having a full carrier queue is forced to recirculate through the entire system, possibly multiple times, until a place becomes available in the preselected queue. In this example, the carrier is diverted into the next available automated dispensing station queue, and is mated to the next prescription-filled container on the exit conveyor 34 for that dispensing unit.

In the present example, as a carrier advances from the carrier queue lane 32 toward the output end of the filled container exit conveyor 34, it passes across an RFID Reader 68, which transmits the carrier identify information to the computer 80. If the queue is a manual one, a label is generated for the filled container and a technician scans the bar-code on the patient-specific label as well as the NDC on the medication container. The scanner transmits the bar code and NDC to the computer 80, which mates the carrier RFID to the bar code and NDC information. The technician then places the labeled container into the container carrier, pushing the carrier with the filled and labeled prescription onto the main conveyor lane to proceed downstream to an as-dispensed imaging queue or pharmacist verification station 26. The manual dispense technician is then free to begin dispensing the next prescription into a container 12, whether or not a carrier has arrived to receive the prescription-filled container.

At the automated dispensing stations 20, the RFID of a container carrier is read as previously described. The control system 19 next verifies that the patient-specific barcode on the next filled container on the exit conveyor matches the order identifier that has just been assigned to the carrier and commands the pick and place unit 52 to place the filled container 12 into the container carrier 14. The carrier with the labeled container is then automatically diverted onto the main conveyor lane 24 for conveyance downstream to an as-dispensed imaging subsystem or directly to a pharmacist for verification at the verification station 26. The next carrier in the queue at the automated dispensing station is then able to advance across the RFID reader and the process is repeated.

Once the carriers with the filled and labeled containers have been imaged and/or verified, they are automatically diverted back into the main conveyor lane 24 for conveyance downstream to the capping station 28 for automatic capping, which may also include application of a safety seal. Once capped, the containers in their mated carriers are automatically diverted back into the main conveyor lane 24 for conveyance downstream to the order accumulation loop 30. The filled, capped containers are then separated from the carriers at an automated packer or order accumulation area. This area may be configured to merge with another conveyance system, for example, a tote line. The empty carrier then advances across a reader that divorces the patient prescription order from the carrier 14 and allows it to repeat the process of associating with a new prescription-filled container 12 at a new dispensing location 20 or 22.

All consumer and/or patient orders are entered into the control system computer 80 and are delivered to each of the automatic dispensing stations 20 and the manual dispensing stations 22 in a balanced fashion. Unmated carriers are delivered to dispensing units having open carrier queue space. In this manner, there may be any number of points of induction of containers into the system by dispensing medications into an empty container and then labeling the container at the dispensing station. Carriers are mated to a particular prescription only as they reach the RFID reader in the fill position at the dispensing unit.

In this manner, As long as a dispensing unit has command instructions from the control system 19 to dispense orders of the medication contained in its magazine, the dispensing unit will always be able to fill and label the next order and mate it to the next received carrier. Advantageously, the system and method eliminate the need for a dispensing unit to wait for arrival of a particular, pre-identified carrier or container.

In another exemplary method of use, container carriers 14 are not employed, and the system 10 may or may not include carrier queue lanes 32 and their associated sensors. In other respects, the system and method of use is substantially similar. Each dispensing station 20 and 22 includes a supply of containers 12 and a supply of one or more products and is available for dispensing one of its stored products into a container and labeling the container. Upon command from the control system 19, a specified quantity of the specified product is automatically or manually dispensed into an empty container 12. Once the container has been filled, it is labeled and deposited onto an exit lane 32 for discharge onto the main conveyor lane 24 and conveyance downstream to the verification station 26 and capping station 28.

It is to be understood that while certain forms of the product dispensing system and method with redundant container induction have been illustrated and described herein, the invention is not to be limited to the specific forms or arrangement of parts described and shown.

The following is claimed as new and desired to be secured by Letters Patent:

1. An automated prescription dispensing method comprising the steps of:
   a. providing a plurality of dispensing stations for dispensing medications, the dispensing stations each including a container magazine containing a quantity of empty fillable containers; a plurality of product magazines, each product magazine containing a quantity of medication; and a labeler;
   b. providing a plurality of container carrier queue lanes each configured to store a plurality of empty carriers, each of the plurality of container carrier queue lanes adjacent to a corresponding one of the plurality of dispensing stations;
   c. providing a computerized dispensing control system having a stored patient order for a medication or a plurality of different medications;
   d. the computerized dispensing control system directing a subset of the plurality of empty carriers into one of the plurality of container carrier queue lanes adjacent to one of the plurality of dispensing stations;
   e. selected ones of the dispensing stations each dispensing a selected quantity of a selected one of the dispensable medications into an empty fillable container in accordance with the patient order stored in the computerized dispensing control system;
   f. next, the selected dispensing stations applying a patient-specific prescription order-identifying label to the filled container, thereby assigning the filled container to the patient order;
   g. the selected dispensing stations discharging the filled, labeled container into a corresponding empty carrier in a corresponding container carrier queue lane, the container carrier queue lane dispensing the combined filled, labeled container and carrier onto a transport conveyor; and
   h. the transport conveyor transporting the combined filled, labeled container and carrier to an accumulation area for accumulating the dispensed medication filled containers to fulfill the patient order.

2. The automated prescription dispensing method of claim 1, wherein each of the plurality of empty carriers includes a carrier identification code, the method further including the step of:
   a. the dispensing stations reading the carrier identification code and mating the carrier identification code with the patient-specific prescription order-identifying label to the patient order.

3. The automated prescription dispensing method of claim 2, wherein the dispensing stations include a carrier scanner reading the identification code of the carrier from a radio frequency identification chip on the carrier.

4. The automated prescription dispensing method of claim 1, wherein:
   a. The plurality of dispensing stations includes an automatic dispensing station and a manual dispensing station; and
   b. the computerized dispensing control system includes a user interface communicating dispensing instructions to the manual dispensing station.

5. The automated prescription dispensing method of claim 1, including the step of:
   a. providing a verification station disposed downstream from the dispensing station, the verification station verifying the label information with the patient order stored in the computerized control system.

6. The automated prescription dispensing method of claim 5, including the step of:
   a. providing a capping station disposed downstream from the verification station, the capping station applying a cap to the filled container.

7. An automated product dispensing system comprising:
   a. a plurality of automated dispensing stations, each dispensing station including a container magazine containing a quantity of empty fillable containers;
   b. each dispensing station including a plurality of product magazines, each product magazine containing a quantity of a preselected product;
   c. a computerized dispensing control system having a stored custom order for a plurality of different products;
   d. a plurality of container carrier queue lanes each configured to store a plurality of empty carriers, each of the plurality of container carrier queue lanes adjacent to a corresponding one of the automated plurality of dispensing stations;

e. the computerized dispensing control system directing a subset of the plurality of empty carriers into one of the plurality of container carrier queue lanes adjacent to one of the plurality of dispensing stations;

f. each dispensing station dispensing a preselected quantity of a selected one of the preselected products into an empty container in accordance with the custom order;

g. the dispensing station including a label unit, the label unit next applying to each filled container a scannable label thereby assigning the filled container to the custom order;

h. the dispensing station discharging the filled, labeled container into a corresponding empty carrier in a corresponding container carrier queue lane, the container carrier queue lane dispensing the combined filled, labeled container and carrier onto a transport conveyor; and i. the transport conveyor transporting the combined filled, labeled container and carrier from the dispensing station to an accumulation area for accumulating the dispensed, product filled containers to fulfill the custom order.

8. The automated product dispensing system of claim 7, further including:

a. the transport conveyor transporting to each dispensing station a quantity of container carriers for receiving the filled containers, each carrier including an identification code;

b. a label scanner disposed to read the scannable label of the filled containers; and c. a carrier scanner disposed to read the identification code of each carrier and mate the carrier identification code with the scannable label of the filled container and assign it to the custom order associated with a container as it is received by the carrier.

9. The automated product dispensing system of claim 8, wherein the carrier scanner reads the identification code of the carrier from a radio frequency identification chip on the carrier.

10. The automated product dispensing system of claim 7, further including a manual dispensing station having:

a. a container magazine including a quantity of empty fillable containers;

b. a plurality of product magazines, each product magazine including a quantity of product;

c. a label device configured for application of an order-identifying label to each container after it has been filled with a selected product; and d. the computerized control system having a user interface communicating dispensing instructions to the manual dispensing station.

11. The automated product dispensing system of claim 7, wherein the plurality of products further comprises a plurality of medications.

12. An automated product dispensing method comprising the steps of:

a. providing an automated dispensing system for dispensing a plurality of products, the dispensing system having a plurality of dispensing stations, each station having a container magazine containing a quantity of empty fillable containers; a plurality of product magazines, each product magazine containing a quantity of a product; and a labeler;

b. providing a plurality of container carrier queue lanes each configured to store a plurality of empty carriers, each of the plurality of container carrier queue lanes adjacent to a corresponding one of the plurality of dispensing stations;

c. storing a product order for a plurality of products in a computerized control system;

d. the computerized dispensing control system directing a subset of the plurality of empty carriers into one of the plurality of container carrier queue lanes adjacent to one of the plurality of dispensing stations;

e. the control system instructing selected ones of the dispensing stations to dispense a selected quantity of a selected one of the products into an empty fillable container in accordance with the product order stored in the computerized dispensing control system;

f. next, the dispensing station labeler applying a product order-identifying label to the filled container, thereby assigning the filled container to the product order;

g. the dispensing station discharging its filled, labeled container into a corresponding empty carrier in a corresponding container carrier queue lane, the container carrier queue lane dispensing the combined filled, labeled container and carrier onto a transport conveyor; and h. sensors verifying the order-identifying label information on each filled, labeled container with the respective product order stored in the computerized control system.

13. The automated product dispensing method of claim 12, wherein each of the plurality of empty carriers includes a carrier identification code, the method further including the step of:

a. the dispensing stations reading the carrier identification code and mating the carrier identification code with the patient-specific prescription order-identifying label to the product order.

14. The automated product dispensing system of claim 13, wherein the dispensing stations include a carrier scanner reading the identification code of the carrier from a radio frequency identification chip on the carrier.

15. The automated prescription dispensing method of claim 12, wherein:

a. The plurality of dispensing stations includes an automatic dispensing station and a manual dispensing station; and b. the computerized control system includes a user interface communicating dispensing instructions to the manual dispensing station.

16. The automated prescription dispensing method of claim 12, including the step of:

a. providing a verification station disposed downstream from the dispensing station, the verification station verifying the label information with the predetermined order stored in the computerized control system.

17. The automated prescription dispensing method of claim 16, including the step of:

a. providing a capping station disposed downstream from the verification station, the capping station applying a cap to the filled container.

* * * * *